(12) United States Patent
Prionas et al.

(10) Patent No.: US 10,022,565 B2
(45) Date of Patent: Jul. 17, 2018

(54) EXTERNAL BEAM RADIOTHERAPY AND IMAGING WITH RADIOACTIVE ISOTOPE

(71) Applicants: Varian Medical Systems, Inc., Palo Alto, CA (US); THE REGENTS OF THE UNIVERSITY OF CALIFORNIA, Oakland, CA (US)

(72) Inventors: Stavros Prionas, Menlo Park, CA (US); Michael C. Green, Palo Alto, CA (US); Edward Seppi, Portola Valley, CA (US); Larry D. Partain, Los Altos, CA (US); James Clayton, Saratoga, CA (US); Stanley Mansfield, Sunnyvale, CA (US); John Boone, Folsom, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 15/206,352

(22) Filed: Jul. 11, 2016

(65) Prior Publication Data
US 2016/0317839 A1    Nov. 3, 2016

Related U.S. Application Data

(63) Continuation of application No. 12/176,974, filed on Jul. 21, 2008, now Pat. No. 9,387,342.

(51) Int. Cl.
*A61N 5/10*    (2006.01)

(52) U.S. Cl.
CPC ............. *A61N 5/1084* (2013.01); *A61N 5/10* (2013.01); *A61N 5/1048* (2013.01); *A61N 5/1081* (2013.01)

(58) Field of Classification Search
CPC ....... A61N 5/10; A61N 5/1081; A61N 5/1084
See application file for complete search history.

(56) References Cited

U.S. PATENT DOCUMENTS 5,189,687 A    2/1993  Bova et al.
5,448,611 A    9/1995  Kerjean
(Continued)

FOREIGN PATENT DOCUMENTS

WO    WO2008106468 A1    9/2008

OTHER PUBLICATIONS

Rivard et al., "Peripheral Brachytherapy, Dosimetry, and Image Guidance Using the AccuBoost System," Medical Physics, Jun. 2007, vol. 34, No. 6, p. 2480.

*Primary Examiner* — Christine H Matthews
(74) *Attorney, Agent, or Firm* — Houst Consulting

(57) ABSTRACT

A method of delivering external radiation beams to a target volume in a body portion includes positioning a radioactive isotope source at a plurality of locations spaced apart around the body portion, and collimating radiation beams of the radioactive isotope source from the plurality of locations, whereby the target volume in the body portion is deposited with a predetermined dose distribution. A radiation device employs a member having a configuration adapted to surround a body portion to be irradiated. The member has a channel and a plurality of collimators spaced apart along and coupled to the channel. The plurality of collimators define a plurality of dwelling locations for a radioactive isotope source in the channel and are configured to collimate radiation beams of the radioactive isotope source.

11 Claims, 7 Drawing Sheets

(56) References Cited

U.S. PATENT DOCUMENTS

| | | |
|---|---|---|
| 7,643,661 B2 | 1/2010 | Ruchala et al. |
| 8,788,017 B2 * | 7/2014 | Yu ........................ A61N 5/1084 378/41 |
| 9,387,342 B2 * | 7/2016 | Prionas .................... A61N 5/10 |
| 2006/0183959 A1 | 8/2006 | Sioshansi et al. |
| 2006/0183960 A1 | 8/2006 | Sioshansi et al. |
| 2008/0230074 A1 | 9/2008 | Zheng et al. |

* cited by examiner

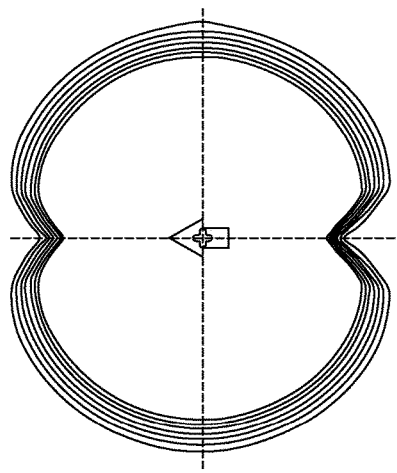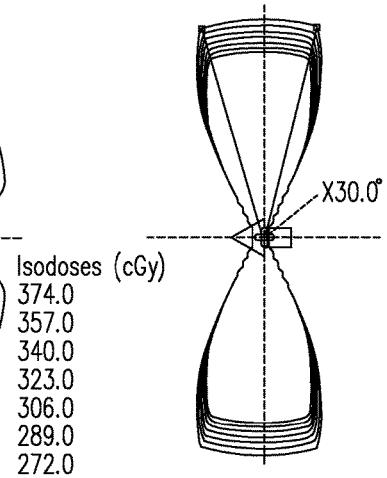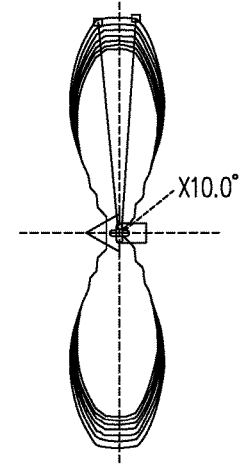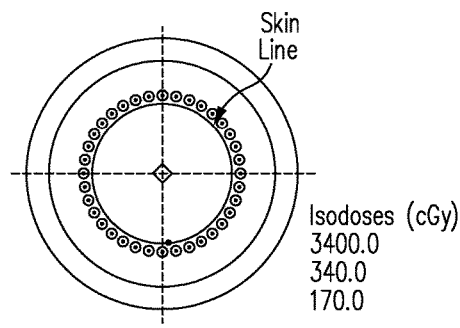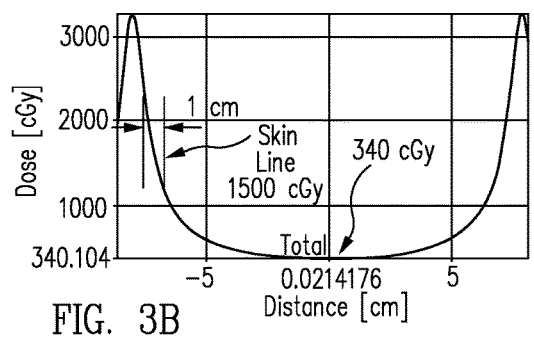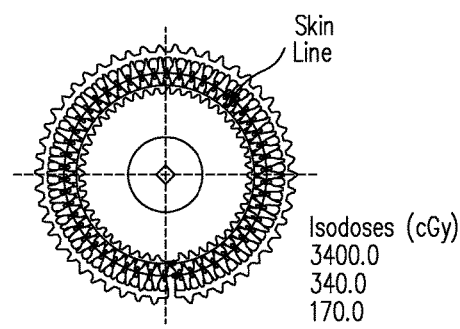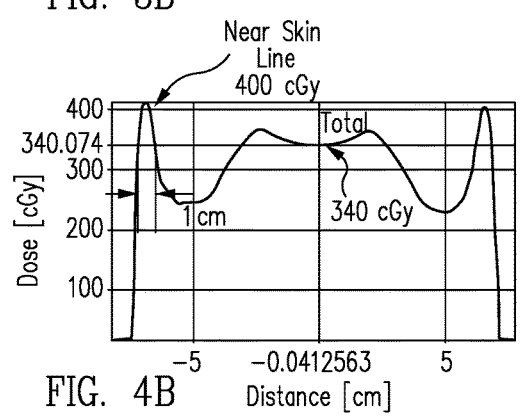

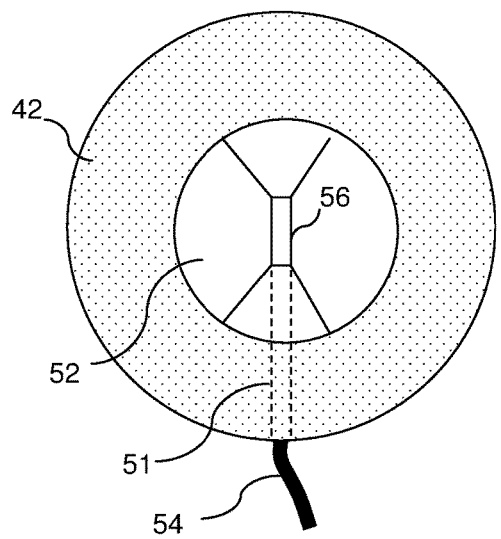
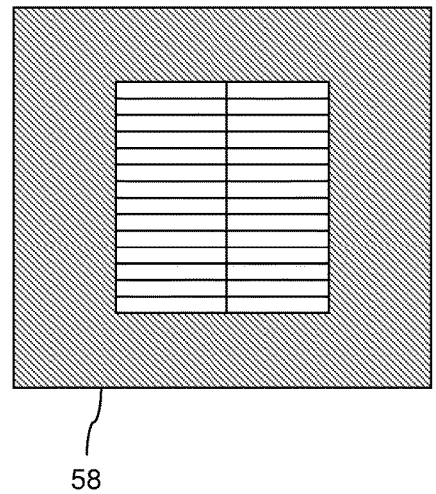
FIG. 14　　　　　　FIG. 15
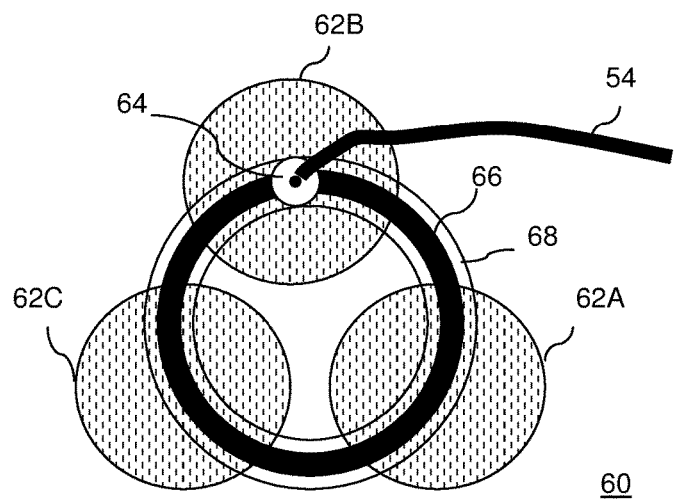
FIG. 16

EXTERNAL BEAM RADIOTHERAPY AND IMAGING WITH RADIOACTIVE ISOTOPE

TECHNICAL FIELD

This invention relates in general to radiation therapy and imaging of timorous tissues and in particular to methods and apparatuses for external beam radiation therapy and imaging using radioactive isotopes.

BACKGROUND

Breast cancer is the most common cancer except for skin cancer among women in the United States. Each year, more than 200,000 American women are diagnosed to have breast cancer. Depending on the type, stage of the cancer and other factors, patients with breast cancer may be treated by surgery, radiation, and other forms of therapy. Surgery involves removal of breast lumps (lumpectomy) or all of the breast tissue (mastectomy). Radiation therapy uses high-energy radiation such as X-rays or gamma rays to destroy cancer cells. Radiation therapy may be used either alone or in conjunction with surgery, chemotherapy or other forms of therapy. Most patients receive radiation therapy after lumpectomy to destroy cancer cells that may remain in the area after lumpectomy. Some patients receive radiation therapy before surgery to shrink the tumor to a manageable size to enable surgical excision.

Various types of radiation therapy are known. Brachytherapy, or internal radiation therapy, involves invasive placement of radioactive substances directly into the breast tissue adjacent to the tumor. Surgical procedures are required to place e.g. catheters into the breast to help guide radioactive materials into the correct area of the breast.

Conventional external beam radiation therapy employs a radiation source outside the body to deliver high energy radiation to the tumor. The radiation source typically includes a relatively large accelerator and electronics, making it difficult to be positioned close to the body for highly localized therapy such as accelerated partial breast irradiation. In addition, because external radiation beam must pass through the skin to reach the tumor, the skin is necessarily subjected to, and often higher, radiation dose than the tumor. Depending on the severity of the skin toxicity of radiation, the resultant damages include erythema (reddening of the skin), which may cause patient discomfort, and desquamation (ulceration and denudation of the skin), which is painful and often requires that the therapy be interrupted.

SUMMARY

The present invention provides improved methods and systems for external beam radiation therapy and imaging using radioactive isotope sources of x-ray or gamma ray photons. The provided methods and systems can deliver a desired dose profile inside the skin, including uniform dose levels throughout the breast, or enhanced dose levels to the cancer, while spreading the skin entry dose from the radiotherapy beam over a large area of the skin to reduce skin toxicity.

In one provided method, a radioactive isotope source is provided at a plurality of locations that are spaced apart, preferably approximately evenly around the body portion. The radiation beams of the radioactive isotope source are collimated at the plurality of locations such that the target volume in the body portion is deposited with a predetermined or desired dose distribution. The predetermined dose distribution may include a dose distribution with a maximal dose in the target volume, a dose distribution with a maximal dose along the periphery of the target volume, a dose distribution substantially uniform in the target volume, and a dose distribution that is substantially higher in the target volume than at the skin surface of the body portion.

The number of the dwell locations for the radioactive isotope source may range from 2 to 360. The radioactive isotope source may be positioned at the plurality of locations by moving the source sequentially to each of the locations. Alternatively, the radioactive isotope sources may be embedded at the plurality of locations such that radiation beams can be delivered from the plurality of locations at a same time.

In another aspect a radiation device is provided. The radiation device includes a member having a configuration adapted to surround a body portion to be irradiated. The member is provided with a channel and a plurality of collimators spaced apart along and coupled to the channel. The collimators are in photon flux communication or coupling with the channel. As used herein and hereafter, the phrase "in photon flux communication or coupling" refers to that at least a portion of photons of a radiation beam pass from the channel to the collimators. The plurality of collimators define a plurality of dwelling locations for the radioactive isotope source in the channel and are configured to collimate radiation beams passing therethrough such that when in use a target volume in a body portion is deposited with a predetermined radiation dose distribution. The member may have a generally annular or elliptical configuration with an opening adapted to surround a patient's uncompressed body portion such as a breast. As used herein and hereafter, the term "uncompressed breast" or "uncompressed body portion" refer to a breast or a body portion that is not compressed or squeezed in a manner that deforms the breast or body portion in its natural or pendulous condition. By way of example, a patient's breast is uncompressed when the patient is in a prone position and the breast is in its natural or pendulous condition. The collimators may be in the form of truncated cone which defines a collimation angle ranging from 1 to 90 degrees. Two to ninety or more collimation cones may be provided in the member.

In a further aspect a radiation apparatus is provided. The radiation apparatus comprises a structure adapted to support a body and provided with an opening to allow a body portion to be irradiated passing through, and a member having a configuration adapted to surround the body portion. The member is provided with a channel and a plurality of collimators spaced apart along and coupled to the channel. The plurality of collimators define a plurality of dwelling locations for one or more radioactive isotope sources in the channel and are configured to collimate radiation beams passing therethrough such that when in use a target volume in the body portion is deposited with a predetermined radiation dose distribution. The member may be movable relative to the body portion, or preferably rotatable about an axis of the body portion in operation.

In still another aspect, a radiation apparatus comprises a structure adapted to support a body and provided with an opening to allow a body portion to be irradiated passing through, and a radiation device adapted to be positioned adjacent to the body portion. The radiation device includes a member provided with a channel to be connected to a radioactive isotope source and a single collimator coupled to the channel and adapted to collimate radiation beams of the radioactive isotope source passing therethrough to a target volume in the body portion. The member may be in the form of sphere. The radiation device may include a multileaf collimator positioned in front of the member. The radiation device may be supported by an arm structure rotatable about an axis of the body portion, or supported by a robotic arm movable with translational and/or rotational degrees of freedom. The radiation apparatus may be adapted to carry out radiation therapy of a cancer, or imaging a target volume in the body portion.

In a provided embodiment, a method of delivering external radiation beam to a target volume in a body portion comprises the following steps. A radiation device is positioned relative to the body portion at a first position. The radiation device includes a member provided with a channel and a plurality of collimators spaced apart along and coupled to the channel, where the plurality of collimators define a plurality of dwelling locations for one or more radioactive isotope sources and are configured to collimate radiation beams of the one or more radioactive isotope sources. Radiation beams from the plurality of dwelling locations are delivered to the target volume while the radiation device is at the first position. After a predetermined time period, the radiation device is rotated to a second position. Radiation beams of the radioactive isotope source are delivered to the target volume from a plurality of new dwelling locations while the radiation device is at the second position. The radiation device may be rotated more than once during treatment as desired.

In another provided embodiment, a method of delivering external radiation beam to a target volume in a body portion comprises the following steps. A body is positioned in a radiation apparatus. The radiation apparatus includes a structure adapted to support the body and has an opening configured to allow a body portion to be irradiated passing through. The radiation apparatus further includes a member which is provided with a channel to be connected to a radioactive isotope source and a single collimator in photon flux communication with the channel. The collimator is configured to collimate radiation beams of the radioactive isotope source passing therethrough to a target volume in the body portion. The radiation apparatus may also include a multileaf collimator placed in front of the member. The member is positioned at a first position to deliver radiation beams of the radioactive isotope source to the target volume from the first position. The member may be rotated from the first position to a second position, and during at least a portion of the rotation, radiation beams of the radioactive isotope source are delivered to the target volume. The rotation from the first position to the second position may constitute a full rotation in about 360 degrees or a partial rotation in any degrees less than 360 degrees. Radiation beams of the radioactive isotope source may be delivered to the target volume at one or more intermediate positions of the member between the first and second positions.

BRIEF DESCRIPTION OF THE DRAWINGS

These and various other features and advantages of the present invention will become better understood upon reading of the following detailed description in conjunction with the accompanying drawings and the appended claims provided below, where:

FIG. 1 is a simulation plot illustrating an omnidirectional distribution of exposure rates from the center of an Ir-192 source as a function of azimuthal angle and distance from the center;

FIG. 2A is a simulation plot illustrating the impact of 30° collimation of an Ir-192 source on distribution of exposure rates;

FIG. 2B is a simulation plot illustrating the impact of 10° collimation of an Ir-192 source on distribution of exposure rates;

FIG. 3A is a simulation plot showing a 2D dose profile of an un-collimated Ir-192 source positioned at 36 locations spaced apart around a simulated breast;

FIG. 3B is a plot showing a line dose profile of an un-collimated Ir-192 source positioned at 36 locations spaced apart around a simulated breast;

FIG. 4A is a plot showing a 2D dose profile of an Ir-192 source with 30° collimation and positioned at 36 locations spaced apart around a simulated breast;

FIG. 4B is a plot showing a line dose profile of an Ir-192 source with 30° collimation and positioned at 36 locations spaced apart around a simulated breast;

FIG. 14 is a schematic illustrating a radiation device in accordance with one embodiment of the invention;

FIG. 15 is a schematic illustrating a multileaf collimator that can be used with a radiation device in accordance with one embodiment of the invention;

FIG. 16 is a schematic illustrating multiple radioactive sources that can be used with a radiation system in accordance with one embodiment of the invention.

DETAILED DESCRIPTION OF VARIOUS EMBODIMENTS

Figure 5A:
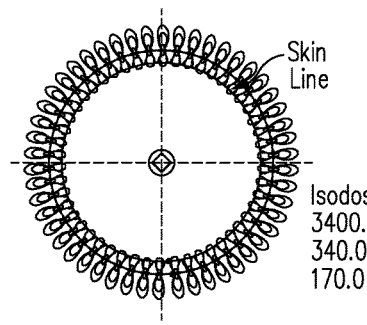
FIG. 5A is a plot showing a 2D dose profile of an Ir-192 source with 10° collimation and positioned at 36 locations spaced apart around a simulated breast.

Various embodiments are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the invention or as a limitation on the scope of the invention. In addition, an aspect described in conjunction with a particular embodiment is not necessarily limited to that embodiment and can be practiced in any other embodiments of the invention. While various embodiments are described below with human breasts, it will be appreciated that the invention can be used on animals as well as humans, and may be used on different body parts.

In general, the invention provides improved external beam radiation therapy and imaging using one or more radioactive isotope sources. The radioactive isotope source(s) is (are) positioned at a plurality of locations ranging e.g. from 2 to 360 locations surrounding a body portion to be irradiated. The radiation beams of the radioactive isotope sources at the plurality of locations are modulated or collimated. The dwell time of the radioactive isotope sources at the plurality of the locations is controlled. By collimating the radiation beams of the radioactive isotope sources, and/or controlling the dwell time of the radioactive isotope sources at each of the plurality of locations, a desired dose distribution in the body portion, or in a target volume of the body portion, can be achieved. For instance, it is desirable to achieve an enhanced dose distribution in the target volume or a significantly low dose distribution in the entry skin area of the body portion, or spread the skin entry dose over a large area to reduce skin toxicity. It is desirable to achieve a uniform and enhanced dose distribution level in the target volume. It is also desirable to have the maximal dose deposited along the periphery of the tumor volume since cancerous cells at the periphery of the tumor are metabolically more active.

Referring to FIGS. 1-7, the concept of some aspects or embodiments of the invention is described without the intention to limit the scope of the invention.

FIGS. 1 and 2 illustrate the distribution of exposure rates of a radioactive isotope source as a function of azimuthal angle and distance from the center of the radioactive source. An Ir-192 source of 5 mm-long is used as an exemplary radioactive isotope source for illustrative purpose. As shown in FIG. 1, the distribution of exposure rates would be omnidirectional if the radiations from the Ir-192 source are not modulated or collimated. This is indicated by the characteristic pattern of geometric anisotropy of the elongated Ir-192 source enclosed in a capsule or cylinder. FIG. 2A and FIG. 2B show the effect of collimation on the radioactive isotope source. With collimations, Ir-192 radiation beams become more directional with beam widths reduced, as shown in FIG. 2A (30° collimation angle) and FIG. 2B (10° collimation angle). The collimation angle will be described in more detail below.

FIGS. 3A, 4A, and 5A illustrate 2D dose profiles of an Ir-192 source spaced 1 cm away from the periphery of a simulated breast (14 cm diameter hemisphere of water). The Ir-192 source dwells at 36 locations that are approximately evenly spaced apart around the periphery of the breast. FIG. 3A shows a 2D dose profile where the Ir-192 radiation beams from 36 locations are not collimated. FIGS. 4A and 5A show 2D dose profiles where the Ir-192 radiation beams are collimated with a 30° and 10° collimation angle respectively.

Figure 5B:
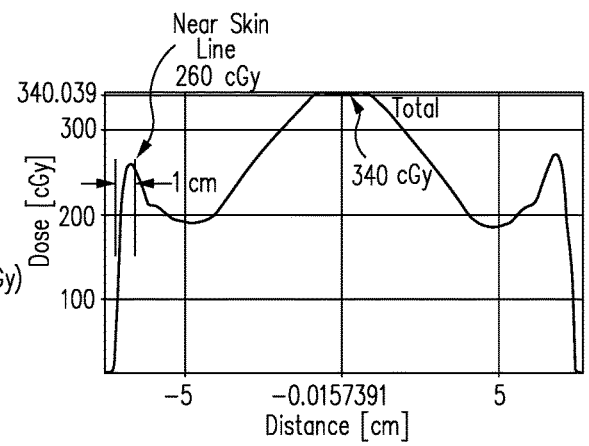
FIG. 5B is a plot showing a line dose profile of an Ir-192 source with 10° collimation and positioned at 36 locations spaced apart around a simulated breast.

FIGS. 3B, 4B, and 5B illustrate line dose profiles corresponding to the 2D dose profiles shown in FIGS. 3A, 4A, and 5A. As shown in FIG. 3B, to achieve a 340 cGy dose level at the center of a breast using an Ir-192 source, the skin dose level would be as high as about 1500 cGy if the Ir-192 radiation beams are not collimated. FIG. 4B shows that with a 30° collimation, the skin dose level would drop to 400 cGy to achieve a 340 cGy dose level at the center of the breast. FIG. 5B shows that with a 10° collimation, the skin dose level would drop further to about 260 cGy with a 340 cGy dose level delivered to the center of the breast.

Figure 6A:
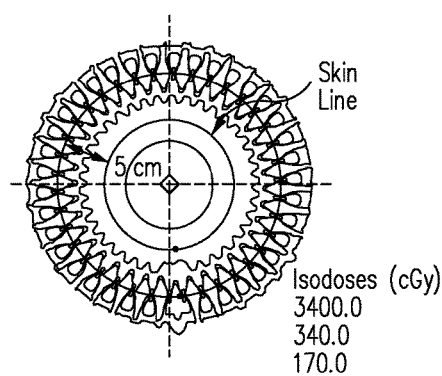
FIG. 6A is a plot showing a 2D dose profile of an Ir-192 source with 30° collimation and spaced approximately 5 cm apart from the surface of the skin.
Figure 7A:
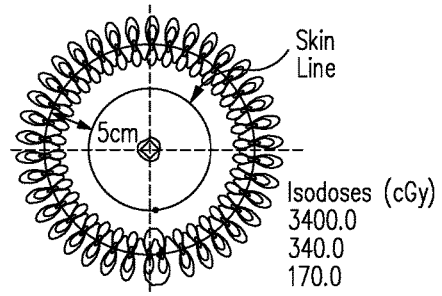
FIG. 7A is a plot showing a 2D dose profile of an Ir-192 source with 10° collimation and spaced approximately 5 cm apart from the surface of the skin.

As additional examples, FIGS. 6A and 7A show 2D dose profiles of an Ir-192 source spaced 5 cm away from the skin of a simulated breast. FIG. 6A shows a 2D dose profile where the radiation beams of Ir-192 source, dwelling at 36 locations proximately evenly spaced apart around the breast, are collimated with a 30° collimation angle. FIG. 7A shows a 2D dose profile where Ir-192 radiation beams are collimated with a 10° collimation angle.

Figure 6B:
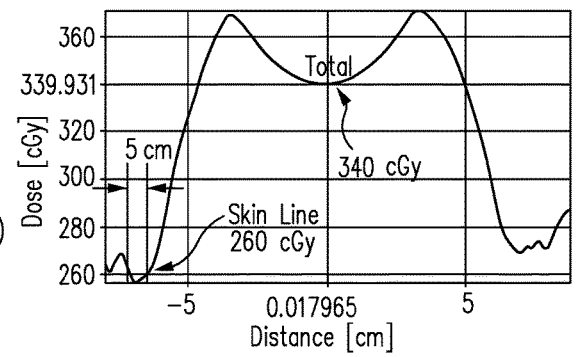
FIG. 6B is a plot showing a line dose profile of an Ir-192 source with 30° collimation and spaced approximately 5 cm apart from the surface of the skin.
Figure 7B:
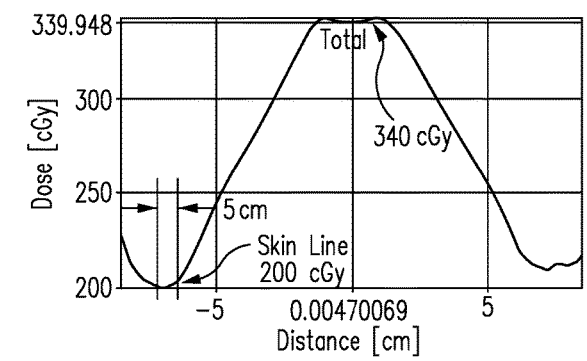
FIG. 7B is a plot showing a line dose profile of an Ir-192 source with 10° collimation and spaced approximately 5 cm apart from the surface of the skin.

As shown in FIG. 6B, to achieve a 340 cGy dose level at the center of the breast, the skin dose level would be about 260 cGy if the radiation beams of Ir-192 source are collimated with 30° collimation. The skin dose level would be dropped to about 200 cGy if the radiation beams of Ir-192 source are collimated with 10° collimation, as shown in FIG. 7B. However, the 50% width of the dose distribution would be reduced from about 11.5 cm to about 8.0 as the collimation angle is reduced from 30° to 10°, as shown in FIGS. 6B and 7B respectively.

Accordingly, a desired dose distribution such as enhanced dose levels in the target volume, or reduced skin entry dose spreading over a large area of the skin, or uniform dose levels throughout the target volume, can be achieved with external radioactive isotope sources by collimating the radiation beams of radioactive isotope sources positioned at a plurality of locations.

Figure 8:
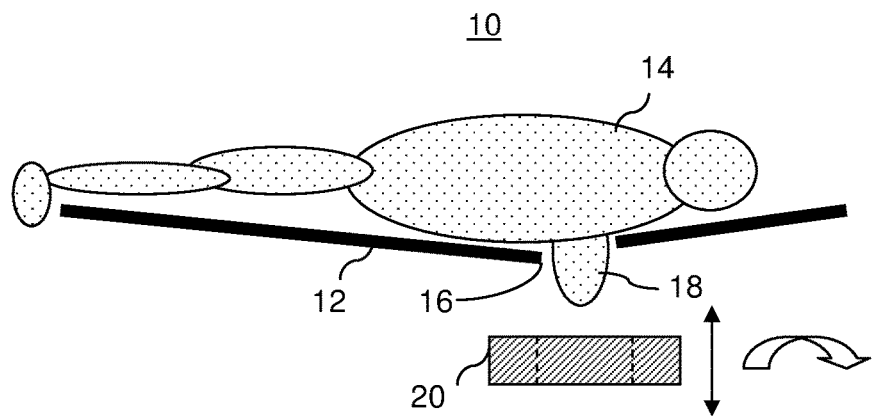
FIG. 8 is a schematic illustrating a radiation system in accordance with one embodiment of the invention.

FIG. 8 illustrates a radiation system 10 that can be used to carry out the method in accordance with one embodiment of the invention. The radiation system 10 includes a structure 12 configured to support a body 14 e.g. a patient in a treatment position such as a prone position. The structure 12 is provided with an opening 16 to allow a body portion 18 such as the patient's breast passing through. A radiation device 20 is positioned adjacent to the body portion 18 to provide a plurality of locations for one or more radioactive isotope sources. The radiation beams are collimated and delivered from the plurality of locations to the body portion or a target volume in the body portion. The radiation device 20 is movable in translational and/or rotational degrees of freedom, as indicated by the arrows in FIG. 8.

Figure 9:
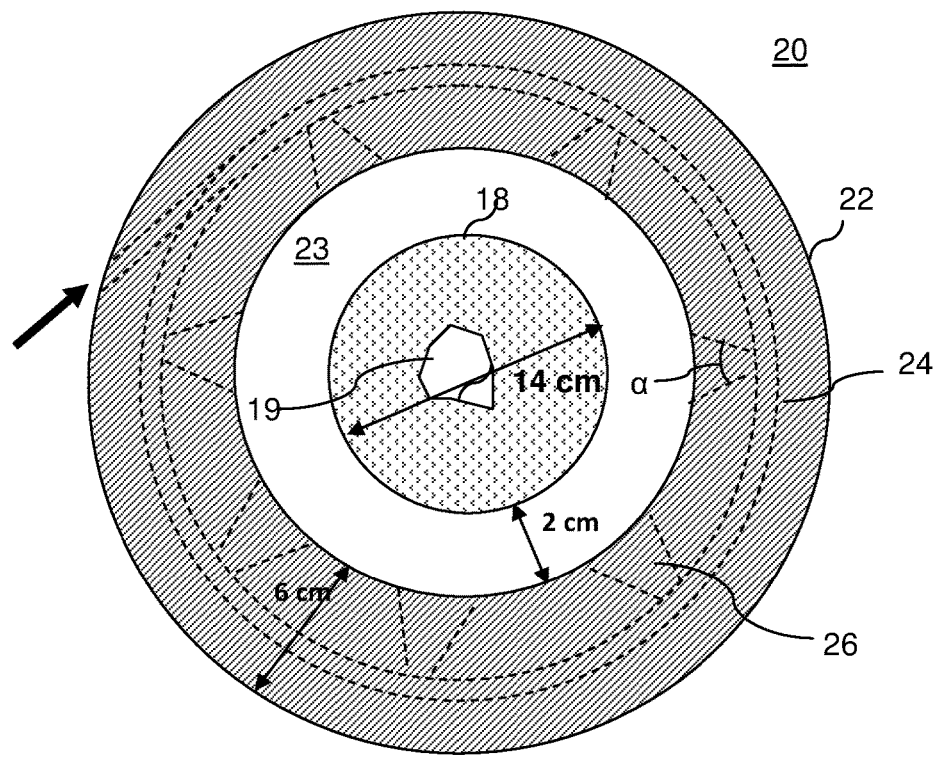
FIG. 9 is a schematic illustrating a radiation device in accordance with one embodiment of the invention.

FIG. 9 schematically shows a radiation device 20 in accordance with one embodiment of the invention. The radiation device 20 includes a member 22 having a configuration suitable for surrounding a body portion 18 to be irradiated. For illustrative purpose, the member 22 shown in FIG. 9 has an annular ring configuration with an opening 23 adapted to surround an uncompressed breast 18 therewithin. The uncompressed breast 18 has a cavity 19 formed by lumpectomy and is approximately centered in or surrounded by the annular member 22. While an annular ring configuration is shown and described, it should be appreciated that other forms of configuration such as cubes or polyhedrons or irregular shapes are possible and anticipated by the inventors.

The member 22 is provided with an internal channel 24 and a plurality of collimators 26. As an exemplary embodiment, the channel 24 is shown as being circular in FIG. 9. The collimators 26 are spaced apart along the channel 24. In some embodiments, the collimators 26 are preferably approximately evenly spaced apart along the channel 24. Depending on the position of the target volume or the nature of the body portion, uneven spacing or other distribution of the collimators 26 along the channel 24 may be desirable. The collimators 26 are coupled to or in photon flux communication with the channel 24. The collimators 26 may be separated from the channel 24 by e.g. windows 28 made of materials substantially transparent to x-rays or gamma rays. The collimators 26 may be in various forms such as truncated cones. The collimators 26 may be open through the inner wall of the member 22 to direct the radiation beams of radioactive isotope sources to the body portion 18 or a target volume 19 in the body portion. The number of the collimators 26 may range from 2 to 90 or more. For example, depending on the type, size, and shape of the body portion or the tumor in the body portion to be treated, 4-72 collimators, or in some embodiments 8-36 collimators, or in some embodiments 12-36 collimators may be spaced apart along the channel 24. By way of example, the number of the collimators 26 can be 2, 4, 7, 9, 12, 18, 36, 60, 72, and so on.

The member 22 is preferably constructed with radiation absorbing materials such that radiations of the radioactive isotope sources not passing through the collimators 26 are substantially blocked or absorbed by the radiation absorbing materials. This would assist in treatment planning by blocking unknown amount of radiation dose to the body portion to be treated or protect the operation personnel of the apparatus from unnecessary exposure. Suitable radiation absorbing materials include high density metals such as tungsten, lead, steel, tantalum, uranium, thorium, iridium, gold, or metal alloys or composites comprising one or more high density elemental metals. In general, the thickness between the outer and inner peripheries of the member 22 is chosen to provide at least 2-3 tenth value layers (TVL) away from the treatment area for good shielding. TVL refers to the thickness of a specified material which when introduced into the path of a given radiation beam, reduces the absorbed dose index to one-tenth. Good shielding is needed for protection of operation personnel and other patient areas that do not need treatment. The following table provides estimated TVL thickness required for some exemplary radioactive isotope sources.

TABLE 1

| Source Material | Lead TVL (mm) | Tungsten TVL (mm) | Steel TVL (mm) |
|---|---|---|---|
| Ir-192 | 7.5 | 3.5 | 25 |
| Cs-137 | 22 | 10 | 53 |
| Co-60 | 40 | 18 | 70 |

The spacing distance between the member 22 and the skin of the body portion 18 to be treated may range from about 0.2 to 10 cm. Positioning the member 22 too close to the body portion 18 may result in excessive skin exposure from the radioactive sources. On the other hand, the radiation dose may fall off if the member 22 is positioned too far away from the body portion 18 and treatment become less effective. For illustrative purpose, FIG. 9 provides an example where the annular member 22 is made of tungsten and has a thickness of about 6 cm. The spacing distance between the annular member 22 and the skin of a breast (of about 14 cm diameter) is about 2 cm. It should be appreciated that numerous variations can be made by one of ordinary skill with respect to the thickness of the annular member, the spacing distance, and the materials used without undue experimentation.

Figure 10:
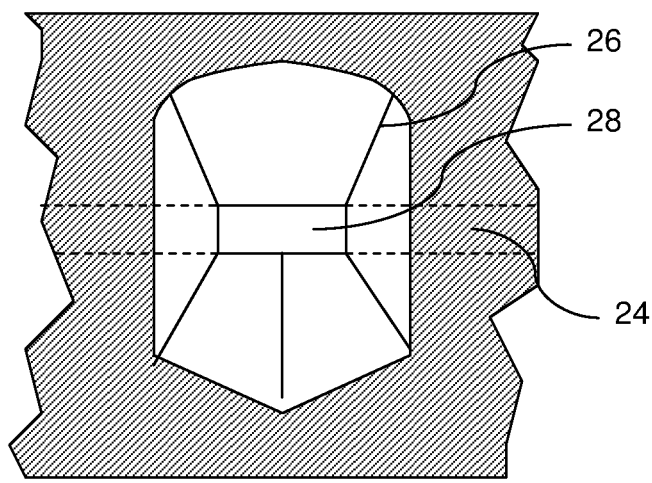
FIG. 10 is a schematic illustrating a partial cross-section of the radiation device shown in FIG. 9.

FIG. 10 illustrates a cross-section of a collimator 26 viewing from the inner surface of the member 22. The shape and size of the collimator 26 can be chosen to provide a predetermined collimation angle ($\alpha$) ranging from 1 to 90°. In some embodiments, a collimation angle ranging from 5° to 45° would be desirable. In some embodiments, a collimation angle ranging from 10° to 30° would be preferable. For example, the collimation angle can be 5°, 10°, 15°, 20°, 25°, 30°, 45°, 60°, 75°, or any suitable degrees between 1 to 90°. In general, a narrow collimation angle provides a more focused beam as compared to a relatively large collimation angle. The collimation angle ($\alpha$) can be chosen in combination with the number of the collimators to provide a desired dose distribution. The collimators may be in the form of collimation cone which may be defined by a continuous surface, or by a plurality of planar surfaces the combination of which forms a generally truncated cone shape. In some embodiments, it would be desirable that the collimation angle of the collimation cones be adjustable. For instance, structures made of radiation absorbing materials such as tungsten cups may be inserted into the collimation cones to change the solid angle or an in-plane angle subtended by the body portion or a target volume in the target portion. In some embodiments, the collimation cones are preferably adjustable by means of such as motors so that the solid angle may be controllably changed or adjusted. This would be advantageous in controlling the overall dose distribution to the breast or body portion. The collimators 26 may be separated from the channel 24 by e.g. windows 28 made of materials substantially transparent to x-rays or gamma rays. Suitable materials for window 28 include those having a low atomic number, or a density equal to or lower than that of water. By way of example, the window 28 can be made of plastics such as methacrylate plastics, carbon fiber composites, solid foams of various materials. The size and shape of the windows 28 may vary based on e.g. the size and shape of the radioactive isotope sources positioned at the window. By way of example, the windows 28 can be in the form of square, rectangle, circle, or ellipse etc.

Radioactive isotope sources are commercially available and can be chosen based on the factors such as x-ray or gamma ray energy level, half-life, cost, and the combination thereof. Radioactive isotope sources producing relatively high energy are preferred for treating deeply seated tumors. Relatively low energy level may be beneficial when used for both imaging and treatment. In general, suitable energy level for treating breast cancer range from 100 to 1500 kV. In some embodiments, orthovoltage energy level (200-500 kV) is preferable. The half-life impacts the shelf life of the products. Suitable radioactive isotopes include Ir-192, Co-60, Cs-131, I-125, Pd-103, Au-198, W-187, Yb-169, Gd-153, Sm-145, Cs-137, Cd-109, Zn-65, Co-58, Co-57, and Co-56. By way of example, Ir-192 provides radiation beams with mean energy level of about 387 KeV and has a half-life of about 74 days. Co-60 provides radiation beams with mean energy level of about 1.25 MeV and has a half-life of about 5 years. The radioactive isotope sources can be in any suitable forms such as cylinders, capsules, plates, lines, and points, etc.

In operation, a radioactive isotope source may be inserted into the channel 24 from the periphery of the member 22, as indicated by the arrow in FIG. 9. The radioactive isotope source may be moved by a cable (not shown) extended into the channel 24. The movement of the cable can be accurately controlled by a computer. An imaging system may be used to monitor the movement and the location of the radioactive isotope source in real time. The radioactive source dwells at a collimator 26 for a predetermined time period. The radiation beam of the source passes through the window 28 and the collimator 26 to the body portion 18. The shape of the radiation beam is collimated by the collimator 26. After a predetermined time period, the radioactive source is moved to the next location for a predetermined time period. This sequential movement continues until the radioactive source dwells at all the predetermined locations for a predetermined time period based on a treatment plan. It should be appreciated that two or more sources, same or different, may be moved concurrently or separately to at least some of the locations.

In an alternative embodiment, a plurality of radioactive sources may be provided or embedded at the plurality of windows 28 such that radiation beams may be delivered to the target volume from a plurality of locations or angles at a same time. The radioactive sources may be same or different. The use of a plurality of sources would significantly reduce treatment time. Shutters (not shown) may be placed between the body portion 18 and the member 22 during the system setup and then removed when the member 22 is properly positioned and/or aligned for operation.

In some embodiments, the member 22 may be movable in translational directions such as moving up and down to position or align the member 22 relative to the body portion 18. The member 22 may also be rotatable to provide more locations from which radiation beams are delivered to the body portion 18. For example, the member 22 may be provided with 9 collimators and radiation beams can be delivered to the body portion 18 from 9 locations when the member 22 is at a first position. The member 22 may then be rotated to a second position, providing 9 additional different locations from which radiation beams can be delivered to the body portion 18. By way of example, the member 22 may rotate three times from an initial position to three different intermediate positions during treatment, providing a total of 36 locations (4×9) from which radiation beams can be delivered to the body portion 18. As another example, rotating a member 22 provided with 25 collimation cones twice would provide a total of 75 locations (3×25) from which radiation beams can be delivered to the body portion 18. In general, 2 to 360 locations may be provided by the combination of the number of collimators provided in the member 22 and rotating the member 22 in operation. For example, in some embodiments, it would be desirable to deliver radiation beams from 8 to 72 locations. In some embodiments, it would be preferable to deliver radiation beams from 12 to 36 locations.

Figure 11:
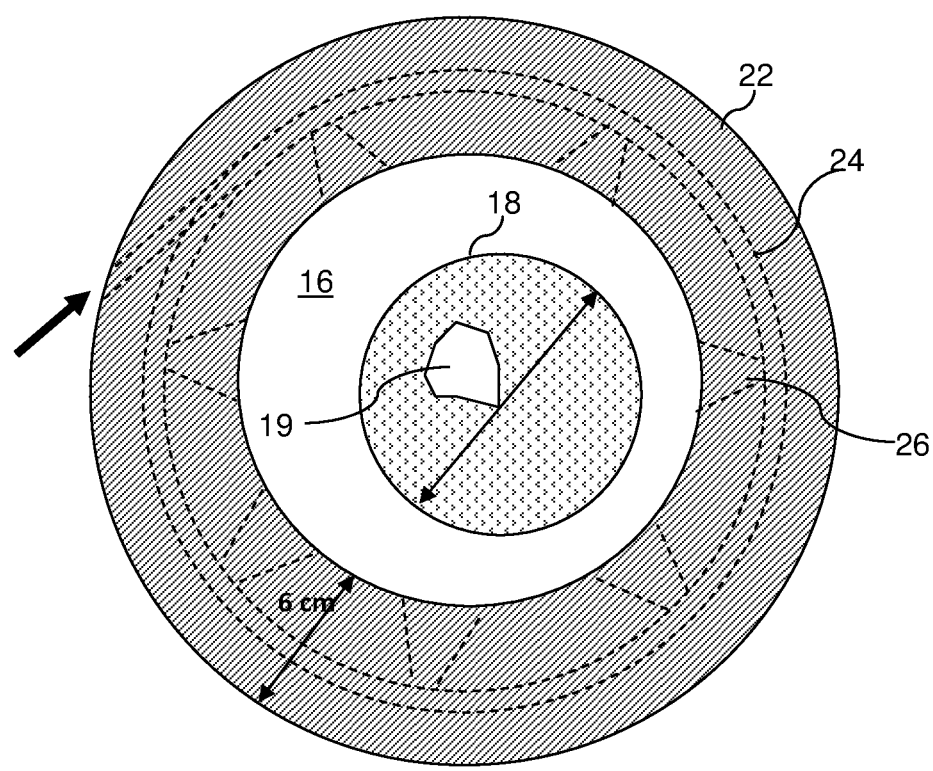
FIG. 11 is a schematic illustrating a radiation device in accordance with another embodiment of the invention.

FIG. 11 illustrates an alternative embodiment where the position of the body portion 18 and/or the member 22 can be adjusted such that a target volume (e.g., a tumor or the tissue adjacent to a lumpectomy cavity) is approximately centered within the plurality of collimation cones.

Figure 12:
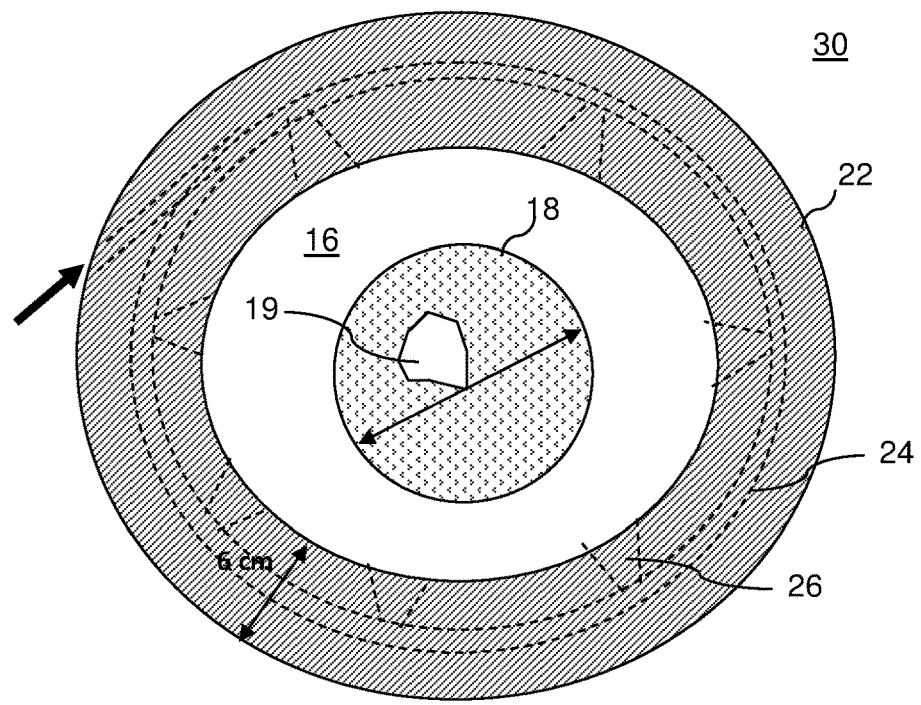
FIG. 12 is a schematic illustrating a radiation device in accordance with a further embodiment of the invention.

FIG. 12 illustrates another alternative embodiment where the member 22 and/or the channel 24 are in a generally elliptic ring configuration. This configuration would provide an elliptical or non-circular moving orbit for a source, or provide a plurality of locations for a plurality of sources along an elliptical channel. The elliptical ring configuration would assist in providing for uniform dose distribution in a target volume and minimize the time required for treating patient.

Figure 13:
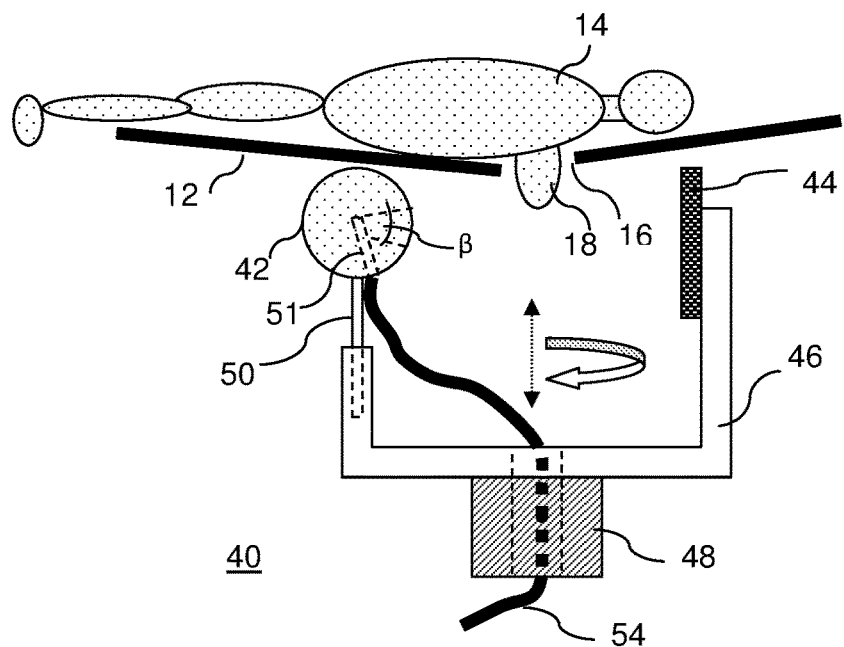
FIG. 13 is a schematic illustrating a radiation system in accordance with one embodiment of the invention.

FIG. 13 illustrates another embodiment of a radiation system 40 in accordance with one embodiment of the invention. The radiation system 40 includes a structure 12 configured to support a body 14 e.g. a patient in a treatment position such as a prone position. The structure 12 is provided with an opening 16 to allow a body portion 18 such as the patient's breast passing through. A radiation device 42 and a detector 44 are positioned opposite each other and supported by an arm structure 46 such as a C-arm. The arm structure 46 may be driven by a motor 48 and rotatable about an axis through the body portion 18 or movable in translation directions such as moving up and down, as indicated by the arrows in FIG. 13. The radiation device 42 is adapted to carry a radioactive isotope source and direct radiation beams of the source to the body portion 18 or a target volume in the body portion 18. The detector 44 can be a digital flat panel imager, and is adapted to receive and measure radiations passing through the body portion 18.

The radiation device 42 can be coupled to the arm structure 46 by a coupling member 50. The coupling member 50 can be moved up and down, tilted, and rotated relative to the arm structure 46 by various means such as bearing, sliders, and motors. Member 50 provides greater versatility for radiation device 42 in combination with the movable arm structure 46.

As shown in FIG. 14, the device 42 is provided with a channel 51 and a collimator 52 in photon flux communication with the channel 51. The channel 51 and the collimator 52 are separated by e.g. a window 56 that is substantially transparent to x-rays or gamma rays. The collimator 52 can be in various suitable forms such as collimation cone. The channel 51 can be configured to be connected to a cable conduit 54 to one or more radioactive isotope sources. Alternatively, a radioactive isotope source can be embedded in the channel 51 such that a source cable is not required. The shape and size of the collimator 52 can be chosen to provide a predetermined collimation angle ($\beta$) ranging from 1 to 90°. In some embodiments, a collimation angle ranging from 5° to 45° would be desirable. In some embodiments, a collimation angle ranging from 10° to 30° would be preferable. For example, the collimation angle can be 5°, 10°, 15°, 20°, 25°, 30°, 45°, 60°, 75°, or any suitable degrees between 1 to 90°. In some embodiments, it would be desirable that the collimation angle of the collimation cones be adjustable. For instance, structures made of radiation absorbing materials such as tungsten cups may be inserted into the collimation cones to change the solid angle or an in-plane angle subtended by the body portion or a target volume in the target portion. In some embodiments, the collimation cones are preferably adjustable by means of such as motors so that the solid angle may be controllably changed or adjusted. The collimator 52 may be defined by a continuous surface, or by a plurality of planar surfaces the combination of which forms a generally cone shape. The size and shape of the window 56 may vary based on e.g. the size and shape of the radioactive isotope materials positioned at the window 56. By way of example, the window 56 can be in the form of square, rectangle, circle, or ellipse etc.

The device 42 can be in any suitable form such as sphere etc. The device 42 can be made of radiation absorbing materials such that radiations from the radioactive isotope sources not passing through the collimator 52 are substantially blocked or absorbed by the radiation absorbing materials. Suitable radiation absorbing materials include high density metals such as tungsten, lead, steel, tantalum, uranium, thorium, iridium, gold, or an alloy or composite comprising one or more high density elemental metals. The device 42 may also include additional shielding layers or materials to provide sufficient protection for operation personnel and other patient areas that do not need treatment. In some embodiments, the device 42 may be constructed relatively small such that it can be easily brought very close to the body portion 18 to be treated. For example, the device 42 can be in the form of a sphere having a diameter ranging from 10 to 20 cm depending on the materials from which the device 42 is constructed. The distance between the device 42 and body portion 18 can be as close as 1 cm or smaller.

The device 42 may also include a multileaf collimator 58 shown in FIG. 15. The multileaf collimator 58 may be placed in front of the device 42. In general, a multileaf collimator 58 includes a plurality of pairs of opposing veins or leaves made of materials that effectively block the radiation of the radioactive source. Each pair of the leaves is controllably movable relative to each other. By driving each leave into different positions, various sizes and shapes of the radiation beam can be formed and the intensity of the radiation beam can be modulated. The use of a multileaf collimator 58 allows many diverse opportunities for optimized dose deliveries, including rapid arc radiation therapy.

The number of leaves in the multi-leaf collimator 58 can have a wide range. Generally, a multileaf collimator 58 having a large number of narrow leaves has a higher resolution than a multileaf collimator 58 having a small number of thick leaves. A high resolution is generally beneficial in shaping the radiation beam precisely to the shape of the tumor and modulating the radiation intensity precisely.

The structure 12 can be in various forms and shapes. For example, the structure 12 can be in curved shape to provide better access for the radiation device 42 to the body portion 18, or provide better tangential view of the body portion 18 in a shorter distance between the radiation device 42 and the body portion 18.

In operation, the patient 14 is positioned on the structure 12 at a treatment position such as a prone position. The radiation device 42 is positioned relative to the body portion 18 by moving, tilting or rotating the coupling member 50 relative the arm structure 46, and/or by moving the arm structure 46 relative to the body portion 18. Once the patient's body portion 18 and the radiation device 42 are at the predetermined positions, a radioactive isotope source is introduced to the channel 51 by a cable conduit 54. Alternatively, a radioactive isotope source may be embedded in the channel 51 such that a cable conduit is not required. Radiation of the radioactive isotope source is modulated by the collimation cone 52, or in combination with the multileaf collimator 58, and delivered to a target volume based on a treatment plan.

The treatment plan for the patient can be established based on the nature, size, shape, and location of the target in the body portion. The treatment plan includes data of the location and orientation of the target with respect to the coordinates of the radiation system established in a pre-treatment session. The treatment plan preferably includes data regarding the radiation doses different portions of the target should receive. Typically, the treatment plan sets forth several treatment sessions or fractions, and includes data regarding the shape of the radiation beam and the time duration the radiation beam should be applied to the target at a plurality of fields during a treatment session. By applying radiation at a plurality of locations, with the shape of the beam optimized to account for the cross sectional shape of the target and other anatomical factors, a conformal dose is delivered.

When a patient is treated in an intensity-modulated radiation therapy (IMRT), the treatment plan may include data regarding the motions of the leaves of the multileaf collimator for each field in the treatment session to achieve intensity-modulated radiation therapy. When each field is being executed, the multiple leaves in the multileaf collimator move according to the IMRT plan so that different portions of the tumor's cross-section receive different amounts of radiation. For example, if one part of the tumor is close to a critical or sensitive structure, the leaves in the MLC beam adjuster may block the radiation near that part during some portion of the field, thereby decreasing the radiation dose received by that part of the tumor and minimizing the possible adverse effect of the radiation exposure by the critical or sensitive structure.

The treatment plan may also include reference data regarding the position of the target, and the relationship between the target movement and the patient's inter- or intra-fraction movement established during a pre-treatment session for image-guided radiation therapy (IGRT). The reference data or the relationship data can be obtained by any suitable imaging techniques such as planar radiography, ultrasound (US), computed tomography (CT), single photon emission computed tomography (SPECT), magnetic resonance imaging (MRI), magnetic resonance spectroscopy (MRS), positron emission tomography (PET), etc. In image-guided radiation therapy, the control module receives data from one or more planar or volumetric imaging devices representing near real time images of the target. The near real time image data are compared with the reference data obtained in the pre-treatment session. The results can then be used to position the patient and/or the radiation source during the treatment session. U.S. Pat. No. 7,227,925 describes a method and system for image-guided radiation therapy, the disclosure of which is incorporated herein by reference in its entirety.

A wide variety of desirable dose distribution can be effectively delivered to a target volume in accordance with the invention. For instance, the radiation device 42 can be positioned relative to the body portion 18 at the first location and radiation beams are delivered to the target volume from the first location. The radiation beams may be modulated by the collimation cone 52 or in combination with the multileaf collimator 58. After a predetermined time period, the arm structure 46 rotates to position the radiation device 42 at a second location from which radiation beams are delivered to the target volume. This rotate-dwell-rotate motion continues until radiation beams are delivered from all predetermined locations each for a predetermined time period based on the treatment plan.

In some embodiments, radiation beams can be delivered to the target volume while the radiation device 42 rotates around the body portion 18 with a constant or varied rotating speed. In some embodiments, the arm structure 46 may rotate the radiation device 42 and move it up or down concurrently such that radiation beams can be delivered to the target volume in a helical trajectory.

In some embodiments, the radiation dose for a treatment fraction may be delivered to a target volume with a single rotation of the radiation device 42. The rotation may be a complete rotation in about 360 degrees or a partial rotation in any degree less than 360 degrees such as 45, 90, 180, 270, or 330 degrees. The rotation of the radiation device 42 may be continuous during which the radiation beams are delivered to the target volume. Alternatively, the rotation may be non-continuous or may operate in an alternating mode of rotate-dwell-rotate as described above. Radiation may be delivered to a target volume when the radiation device 42 rotates, or when the radiation device 42 is stationary. In some embodiments, the radiation dose for a treatment fraction may be delivered to a target volume using the radiation device 42 with more than one rotation.

In some embodiments, two or more same or similar radiation devices 42 may be supported by C-arms. The two or more radiation devices 42 may each carry a same or different radioactive isotope source. For example, two radiation devices 42 may be supported by C-arms and spaced apart by e.g. 180 or 90 degrees. In another example, three radiation devices 42 may be supported by C-arms and spaced apart by e.g. 120 degrees. Radiation beams may be delivered from the two or more radiation devices 42 spaced apart at a same time. The C-arms supporting the two or more devices 42 may be rotated or stationary during treatment. The use of two or more radiation devices 42 would significantly reduce treatment time.

FIG. 16 illustrates another embodiment where storage vaults 62A-62C of multiple, radioactive isotope sources are ganged together such that all their source extraction points 64 can be accessed by rotating a ring 66 through a transport structure 68 when the cable conduit 54 is aligned with a specific source. For example as shown in FIG. 16, three storage vaults 62A-62C of different radioactive isotope sources can be ganged together. The energies of the different radioactive isotope sources are chosen to optimize either or both of treatment delivery and imaging. Higher energy source such as Co-60 can further reduce skin dose toxicity. Lower energy source can produce cone beam CT images with higher soft tissue contrast. Combinations of energies can give higher accuracy CT numbers for better treatment planning and for higher resolution of various contrast and treatment-enhancement agents. By way of example, multiple sources of Ir-192, Co-60, and Cs-131 can be grouped together. Other alternates of sources include I-125, Pd-103, and other suitable isotope sources.

Figure 17:
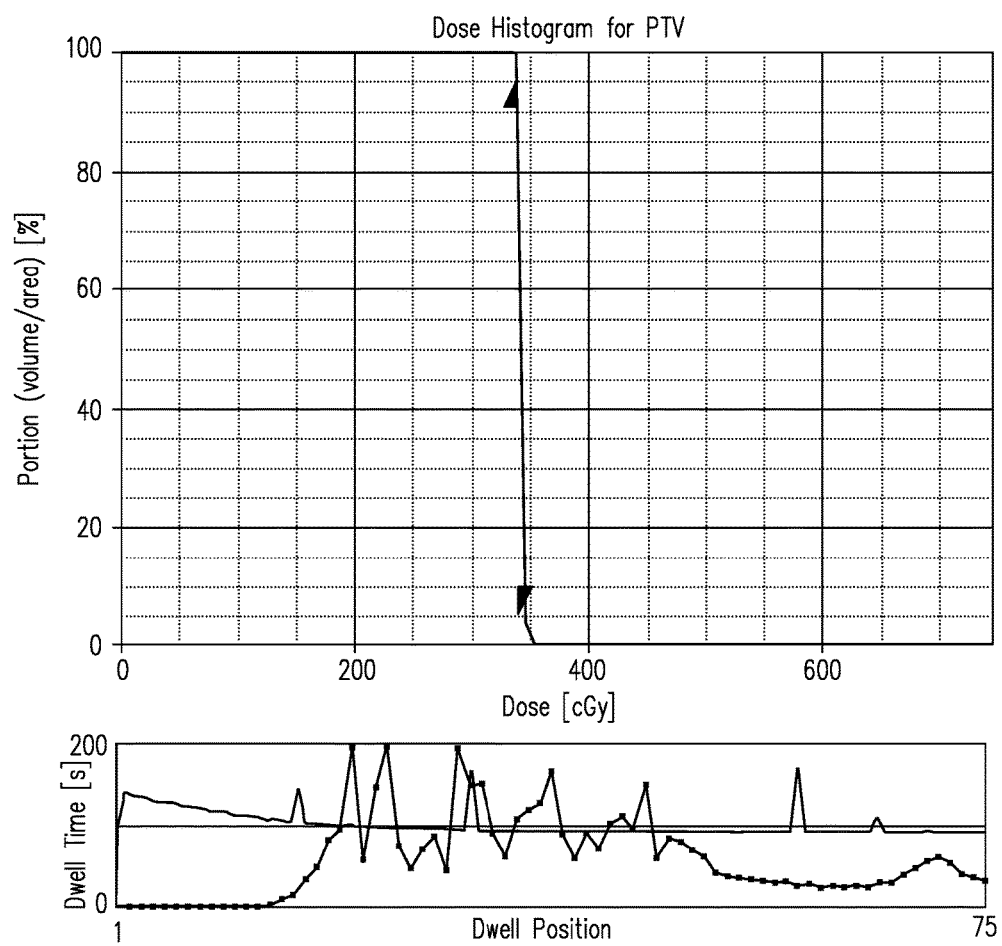
FIG. 17 shows a dose-volume histogram for an optimized dose delivery in accordance with one embodiment of the invention.

FIG. 17 is a dose-volume histogram showing that a nearly perfect flat dose delivery can be achieved in accordance with one embodiment of the invention. In this specific embodiment, a radiation dose of 340 cGy is delivered to a target volume with a diameter of 4 cm eccentrically located inside a simulated uncompressed breast with a diameter of 14 cm. The radioactive isotope source is Ir-192 positioned about 4 cm away from the skin surface. Radiations are delivered from 75 locations approximately evenly spaced apart along a circular orbit. The radiation beam is collimated with a 10° collimation angle. The dwell times from 0 to 200 seconds are shown at the bottom of FIG. 17. This example shows that a desirable dose profile can be delivered to a target volume with radioactive isotope sources from a plurality of locations where the radiation beams and the dwell time are modulated.

From the foregoing it will be appreciated that, although specific embodiments of the invention have been described herein for purposes of illustration, various modifications may be made without deviating from the spirit and scope of the invention. For example, the radiation systems shown in FIGS. 8 and 13 can be used for imaging as well as treatment. The patient can be supported in a supine position or a substantially upright position, as well as a prone position. The radiation device can be supported on a robotic arm that is capable of moving in both translational and rotational degrees of freedom. Further, a gating process may be incorporated in the process of radiation therapy in response to sudden movement of the patient in an abnormal pattern, such as coughing, sneezing, muscle cramping etc. All these or other variations and modifications are contemplated by the inventors and within the scope of the invention.

What is claimed is:

1. A system, comprising:
   a supporting device configured to support a patient; and
   a radiation device configured to deliver external radiation to the patient, wherein the radiation device comprises a body having an opening defining a spatial volume having a generally cylindrical and/or truncated cone shape to allow a portion of the patient on the supporting device to extend into such that the portion of the patient is surrounded by the body when in radiation, the body comprising a plurality of dwelling locations for radioactive isotope sources and a plurality of collimators coupled to the plurality of dwelling locations configured to collimate radiation from the radioactive isotope sources to a treatment target in the portion of the patient,
   wherein at least one of the plurality of collimators comprises a tungsten cup having a collimation angle ranging from 1 to 90 degrees.

2. The system of claim 1, wherein the body of the radiation device comprises a first surface defining a shape of the spatial volume of the body, and a second surface opposite to the first surface, the first and second surfaces defining a thickness of a wall of the body providing the spatial volume, wherein the thickness is chosen to provide at least 2-3 tenth value layers (TVLs).

3. The system of claim 2, wherein the plurality of collimators comprise a passageway in the wall of the body.

4. The system of claim 2, wherein the plurality of collimators are spaced apart in the wall of the body around the spatial volume in 360 degrees.

5. The system of claim 2, wherein at least one of the plurality of collimators in the body of the radiation device provide a collimation angle ranging from 5 to 45 degrees.

6. A method, comprising:
   supporting a patient on a supporting device;
   positioning a radiation device configured to deliver external radiation relative to the patient, wherein the radiation device comprises a body having an opening defining a spatial volume to allow a portion of the patient on the supporting device to extend into such that the portion of the patient is surrounded by the body when in radiation, the body comprising a plurality of dwelling locations for radioactive isotope sources and a plurality of collimators coupled to the plurality of dwelling locations configured to collimate radiation from the radioactive isotope sources to a treatment target in the portion of the patient, wherein at least one of the plurality of collimators comprises a tungsten cup having a collimation angle ranging from 1 to 90 degrees;
   delivering radiation to the treatment target in the portion of the patient; and
   conducting a gating process in response to sudden movement of the patient in an abnormal pattern.

7. The method of claim 6, wherein the spatial volume defined by the body of the radiation device comprises a generally cylindrical and/or truncated cone shape.

8. The method of claim 6, wherein the body of the radiation device comprises a first surface defining a shape of the spatial volume of the body, and a second surface opposite to the first surface, the first and second surfaces defining a thickness of a wall of the body providing the spatial volume, wherein the thickness is chosen to provide at least 2-3 tenth value layers (TVLs).

9. The method of claim 8, wherein the plurality of collimators comprise a passageway in the wall of the body.

10. The method of claim 7, wherein the plurality of collimators are spaced apart in a wall of the body around the spatial volume in 360 degrees.

11. The method of claim 7, wherein at least one of the plurality of collimators in the body of the radiation device provide a collimation angle ranging from 5 to 45 degrees.

* * * * *